United States Patent
Ingmanson

(10) Patent No.: US 10,255,995 B2
(45) Date of Patent: Apr. 9, 2019

(54) SYSTEMS AND METHODS FOR CREDIT-BASED USAGE OF SURGICAL INSTRUMENTS AND COMPONENTS THEREOF

(71) Applicant: Covidien LP, Mansfield, MA (US)

(72) Inventor: Michael D. Ingmanson, Stratford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/482,897

(22) Filed: Apr. 10, 2017

(65) Prior Publication Data

US 2017/0212995 A1 Jul. 27, 2017

Related U.S. Application Data

(63) Continuation of application No. 14/660,990, filed on Mar. 18, 2015, now Pat. No. 9,619,618.

(51) Int. Cl.
*G16H 40/63* (2018.01)
*A61B 17/072* (2006.01)
*A61B 90/98* (2016.01)
*G16H 40/20* (2018.01)
*G06F 19/00* (2018.01)
*A61B 90/00* (2016.01)
(Continued)

(52) U.S. Cl.
CPC ....... *G16H 40/63* (2018.01); *A61B 17/07207* (2013.01); *A61B 90/98* (2016.02); *G06F 19/00* (2013.01); *G16H 40/20* (2018.01); *A61B 1/00062* (2013.01); *A61B 2017/0046* (2013.01); *A61B 2017/00199* (2013.01); *A61B 2017/00221* (2013.01); *A61B 2017/00734* (2013.01); *A61B 2090/0803* (2016.02);
(Continued)

(58) Field of Classification Search
CPC ............ A61B 2090/0803; A61B 90/98; A61B 1/00062; G06Q 20/14; G06Q 30/04; G06Q 20/145; G06Q 20/22; G06Q 20/28
See application file for complete search history.

(56) References Cited

U.S. PATENT DOCUMENTS 5,258,906 A  11/1993  Kroll et al.
5,732,401 A   3/1998  Conway
(Continued)

FOREIGN PATENT DOCUMENTS

| AU | 2014203647 A1 | 7/2014 |
| EP | 2283780 A2 | 2/2011 |
| WO | 2011/032177 A2 | 3/2011 |

OTHER PUBLICATIONS

Extended European Search report issued in corresponding application No. 16160830.2 dated Jul. 11, 2016.

*Primary Examiner* — Christopher Stanford

(57) ABSTRACT

Systems and methods for credit-based usage of surgical instruments include one or more surgical instruments having associated therewith a usage amount, a pre-determined maximum usage amount, and an available usage credit amount that is less than the pre-determined maximum usage amount. The systems implement and the methods include comparing the usage amount to the pre-determined maximum usage amount and inhibiting further use of the at least one reusable component when the usage amount is equal to the pre-determined maximum usage amount, and identifying the available usage credit amount and inhibiting further use of the at least one reusable component when there is no available usage credit remaining.

13 Claims, 6 Drawing Sheets

(51) Int. Cl.
  *G06Q 30/04* (2012.01)
  *A61B 1/00* (2006.01)
  *A61B 17/00* (2006.01)
  *G06Q 10/00* (2012.01)
  *G06Q 20/14* (2012.01)
  *G06Q 20/22* (2012.01)
  *G06Q 20/28* (2012.01)
  *G06Q 50/22* (2018.01)

(52) U.S. Cl.
  CPC ............... *A61B 2090/0808* (2016.02); *A61B 2090/0814* (2016.02); *G06F 19/328* (2013.01); *G06Q 10/20* (2013.01); *G06Q 20/14* (2013.01); *G06Q 20/145* (2013.01); *G06Q 20/22* (2013.01); *G06Q 20/28* (2013.01); *G06Q 30/04* (2013.01); *G06Q 50/22* (2013.01)

(56) References Cited

U.S. PATENT DOCUMENTS

| | | |
|---|---|---|
| 6,092,722 A | 7/2000 | Heinrichs et al. |
| 7,001,330 B2 * | 2/2006 | Kobayashi ......... A61B 1/00059 600/117 |
| 7,115,091 B2 | 10/2006 | Root et al. |
| 7,193,519 B2 | 3/2007 | Root et al. |
| 7,349,856 B2 * | 3/2008 | Ackermann ......... G06Q 20/401 705/2 |
| 7,835,823 B2 | 11/2010 | Sillman et al. |
| 8,351,898 B2 | 1/2013 | Raleigh |
| 8,888,830 B2 | 11/2014 | Dunleavy et al. |
| 9,076,187 B1 | 7/2015 | Laing et al. |
| 9,107,690 B2 | 8/2015 | Bales, Jr. et al. |
| 2002/0120467 A1 | 8/2002 | Buanes |
| 2003/0110260 A1 | 6/2003 | Kuth et al. |
| 2003/0208378 A1 | 11/2003 | Thangaraj et al. |
| 2006/0190048 A1 | 8/2006 | Gerber |
| 2007/0156496 A1 | 7/2007 | Avery et al. |
| 2009/0248578 A1 | 10/2009 | Pollock et al. |
| 2012/0116367 A1 | 5/2012 | Houser et al. |
| 2012/0323597 A1 | 12/2012 | Woolford |
| 2013/0268940 A1 | 10/2013 | Gmach et al. |
| 2013/0293353 A1 | 11/2013 | McPherson et al. |
| 2014/0052135 A1 | 2/2014 | Aman et al. |
| 2014/0074191 A1 | 3/2014 | Dunleavy et al. |
| 2014/0309588 A1 | 10/2014 | Eggert et al. |

* cited by examiner

SYSTEMS AND METHODS FOR CREDIT-BASED USAGE OF SURGICAL INSTRUMENTS AND COMPONENTS THEREOF

CROSS-REFERENCE TO RELATED APPLICATIONS

This is a continuation and claims priority to, and the benefit of U.S. patent application Ser. No. 14/660,990, filed Mar. 18, 2015, the entire contents of which is hereby incorporated by reference.

BACKGROUND

1. Technical Field

The present disclosure relates to surgical instruments and, more particularly, to systems and methods for credit-based usage of surgical instruments and components thereof.

2. Background of Related Art

Surgical instruments may be generally classified as single-use instruments, reusable instruments, partially-reusable instruments (where one or more components are configured for single use and one or more other components are configured for reuse), or limited-use instruments (or limited-use components). Such limited-use instruments or components are classified as such because these instruments or components define useful lives, that is, a period during which use of the instruments or components is determined to be safe and effective. The useful life of a particular instrument or component is typically determined by testing and/or modeling that reflects the effects of the surgical environment on the instrument or component, stresses imparted to or by the instrument or component during use, the impact of sterilization processes on the instrument or component, and/or the normal wear and tear resulting from reuse of the instrument or component. The useful life of an instrument or component may be measured against one or more metrics such as: time from manufacturing, time in actual use, time undergoing sterilization, number of activations, number of procedures, number of sterilizations, number of charge cycles, etc.

Historically, clinicians were required to know (or determine) the useful life of an instrument or component, track usage in accordance therewith, and retire the instrument or component once its useful life had been reached. With the advent of intelligent instruments and components, manual use-tracking by the clinician has been replaced by the manufacturer programming the instrument or component to measure the useful life thereof and disable functionality (partially or fully) when the useful life has been reached.

The useful life of a particular instrument or component may also be helpful in considering the economics of purchasing a particular instrument, e.g., a price-per-procedure value can be determined. On the manufacturer's side, increased prices resulting from the additional costs associated with increasing the usable life of an instrument or component are more easily justified when viewed in a price-per-procedure context.

SUMMARY

To the extent consistent, any of the aspects and features of the present disclosure may be used in conjunction with any or all of the other aspects and features detailed herein.

Provided in accordance with the present disclosure is a surgical system implementing a credit-based usage system. The surgical system includes one or more surgical instruments, each including at least one reusable component having associated therewith a usage amount, a pre-determined maximum usage amount, and an available usage credit amount. The available usage credit amount is less than the pre-determined maximum usage amount. The one or more surgical instruments each further include a processor and a memory storing instructions that, when executed by the processor, cause the processor to compare the usage amount to the pre-determined maximum usage amount and inhibit further use of the at least one reusable component when the usage amount is equal to the pre-determined maximum usage amount, and identify the available usage credit amount and inhibit further use of the at least one reusable component when there is no available usage credit remaining.

In embodiments, the memory further stores instructions that, when executed by the processor, cause the processor to update the usage amount after use of the at least one reusable component.

In embodiments, the memory further stores instructions that, when executed by the processor, cause the processor to update the available usage credit amount after use of the at least one reusable component and update the available usage credit amount in response to receipt of instructions to replenish usage credit. The replenish instructions may be provided in response to the purchase of additional usage credit.

In embodiments, the usage amount, the pre-determined maximum usage amount, and the available usage credit amount are measured in number of uses. Alternatively, the usage amount, the pre-determined maximum usage amount, and the available usage credit amount may be measured in time of use or via any other suitable metric.

In embodiments, the available usage credit amount corresponds to an amount of usage credit purchased.

In embodiments, a first reusable component of the at least one reusable component includes a memory that stores the usage amount, the pre-determined maximum usage amount, and the available usage credit amount for the first reusable component. A second reusable component of the at least one reusable component may also be provided. In such embodiments, the second reusable component may store its one usage information and/or the first reusable component may store the usage amount, the pre-determined maximum usage amount, and the available usage credit amount for the second reusable component in the memory of the first reusable component.

In embodiments, a display screen of the surgical instrument or in communication with the surgical instrument is provided. The display screen is configured to display status information regarding the usage amount, the pre-determined maximum usage amount, and the available usage credit amount.

In embodiments, the system further includes a device in communication with the one or more surgical instruments that is configured to provide instructions to the surgical instrument(s) to modify, e.g., increase or decrease, the available usage credit amount.

In embodiments, the system includes a plurality of surgical instruments. In such embodiments, a device in communication with the plurality of surgical instruments enables the transfer of usage credit between two or more of the plurality of surgical instruments.

A method for credit-based usage of a surgical instrument is also provided in accordance with the present disclosure. The method includes assigning a usage credit amount to at least one reusable component of a surgical instrument that is less than a pre-determined maximum usage amount of the at least one reusable component. The method further includes updating the usage credit amount in response to use of the at least one reusable component and inhibiting further use of the at least one reusable component when there is no available usage credit remaining.

In embodiments, the usage credit amount is assigned to the at least one reusable component in response to purchasing usage credits.

In embodiments, the method further includes replenishing the usage credit amount. In response to replenishing the usage credit amount, further use of the at least one reusable component is permitted.

In embodiments, replenishing the usage credit amount is accomplished via a device in communication with the surgical instrument.

In embodiments, the usage credit amount and the pre-determined maximum usage amount are measured in number of uses. Alternatively, the usage credit amount and the pre-determined maximum usage amount may be measured in time of use or via any other suitable metric.

In embodiments, the method further includes tracking use of the at least one reusable component and inhibiting further use of the at least one reusable component when the at least one reusable component has been used the pre-determined maximum usage amount.

BRIEF DESCRIPTION OF THE DRAWINGS

The present disclosure and its various aspects and features are described hereinbelow with reference to the accompanying drawings, wherein.

DETAILED DESCRIPTION

The present disclosure relates to systems and methods for credit-based usage of surgical instruments which better meet the needs and/or resources of a particular medical facility and more appropriately allocate cost as compared to traditional sales regimes. Although detailed below with respect to particular facilities, systems, instruments, and/or components, the aspects and features of the present disclosure are equally applicable for use with any suitable surgical instrument and/or system and in any suitable facility.

Figure 1:
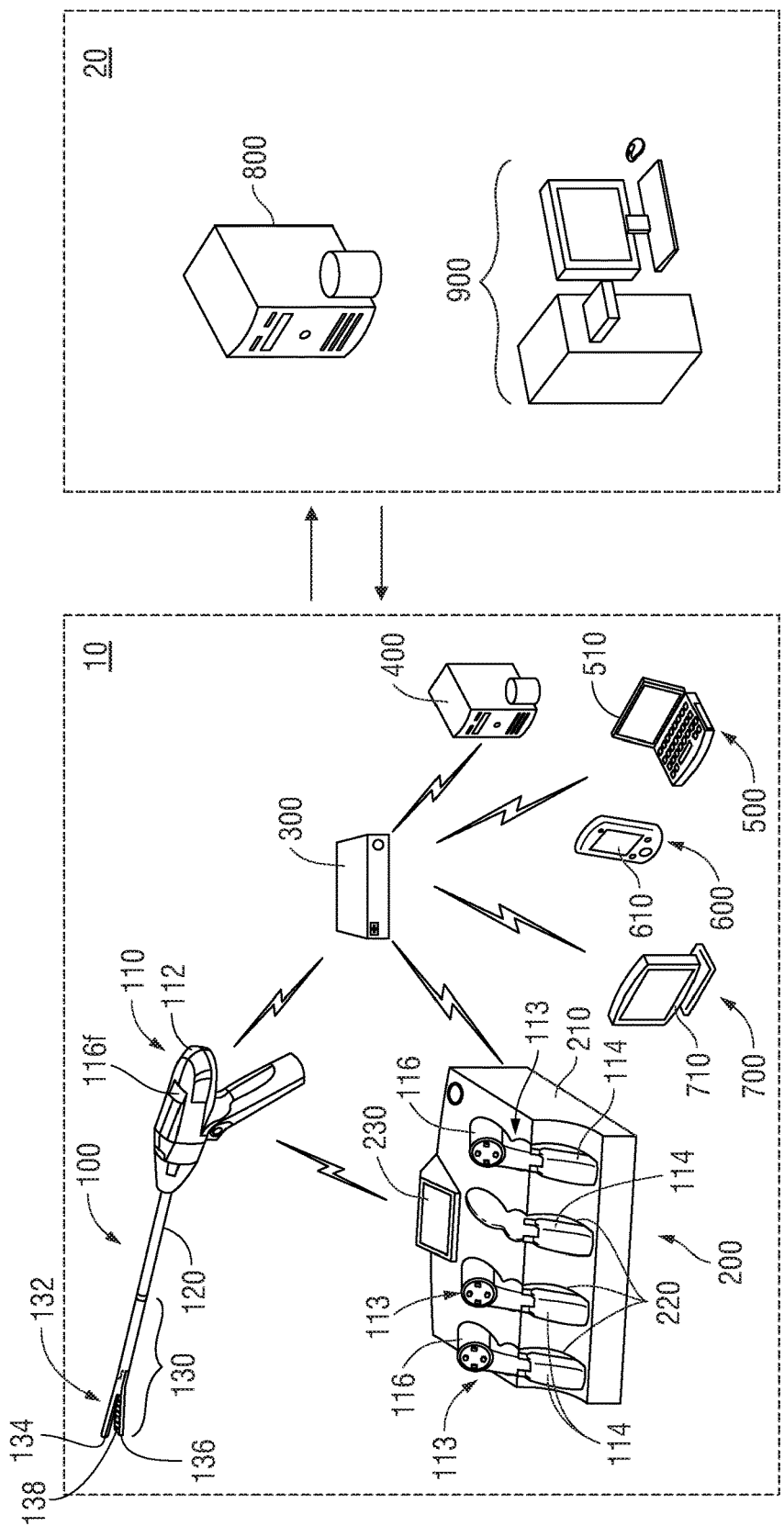
FIG. 1 is a schematic illustration of a system provided in accordance with the present disclosure.

Referring to FIG. 1, a medical facility 10 is shown generally including one or more surgical instruments, e.g., a surgical stapler 100, and a plurality of devices configured for use within medical facility 10, e.g., a charger 200, a router 300, a server 400, a computer 500, a smartphone or tablet 600, a display monitor 700, etc. Surgical stapler 100 and/or one or more of devices 200-700 may further be configured to communicate with a remote facility 20 that includes, for example, one or more servers 800 and/or one or more computers 900.

Surgical stapler 100 is a battery-powered device including a handle assembly 110 configured for selective connection with an adapter 120 which, in turn, is configured for selective connection with an end effector 130. Alternatively, an end effector may be directly connected to handle assembly 110. Handle assembly 110 includes an outer housing 112 that is configured to receive and enclose an inner assembly 113. Inner assembly 113 includes a battery assembly 114 and a power-pack 116. Battery assembly 114 provides power to power-pack 116 for powering surgical stapler 100 while power-pack 116 controls the operation of surgical stapler 100. Adapter 120 interconnects power-pack 116 and end effector 130 and enables mechanical and electrical communication therebetween. End effector 130 includes a tool assembly 132 having an anvil assembly 134 and a cartridge assembly 136. Cartridge assembly 136 is pivotal in relation to anvil assembly 134, although this configuration may be revered, between an open position and a closed position and houses a staple cartridge 138 therein. Upon firing, staples are sequentially ejected from staple cartridge 138 for formation against anvil assembly 134.

Figure 2:
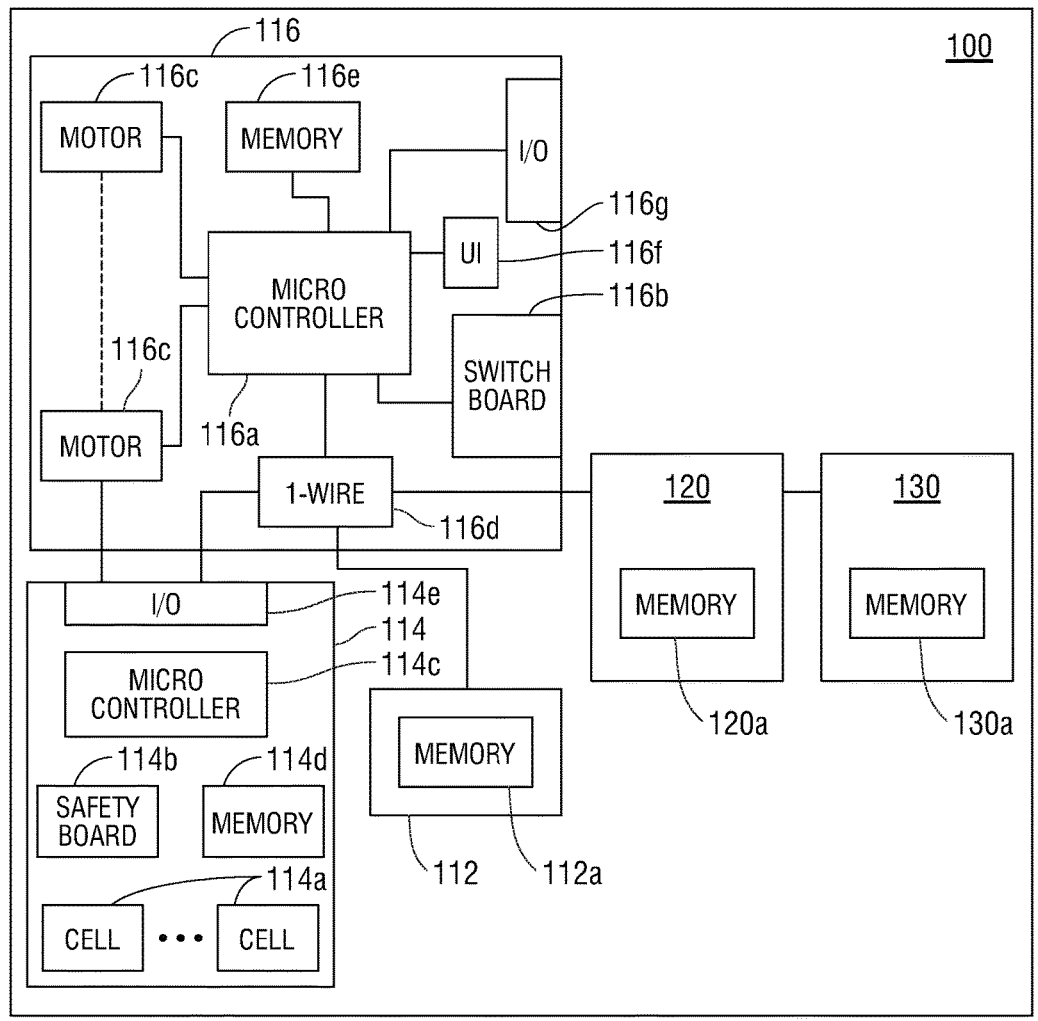
FIG. 2 is a schematic illustration of a surgical instrument configured for use with the system of FIG. 1.

With additional reference to FIG. 2, as noted above, battery assembly 114 provides power to power-pack 116 to power surgical stapler 100. Battery assembly 114 generally includes a plurality of battery cells 114a, a safety board 114b, a microcontroller 114c, a memory 114d, and an input/output 114e. Safety board 114b monitors the charging and discharging of battery cells 114a to ensure safe and proper operation thereof. Microcontroller 114c controls the receipt of energy by battery cells 114a and the delivery of energy from battery cells 114a. Memory 114d stores information relating to battery assembly 114 such as identifying data, status data, and usage data. Input/output 114e enables data and power transmission to/from battery assembly 114.

Power-pack 116, as noted above, controls the operation of surgical stapler 100. Power-pack 116 generally includes a microcontroller 116a, a switch board 116b, a plurality of motors 116c, a 1-wire communication chip 116d, a memory 116e, a user interface 116f, and an input/output 116g. Microcontroller 116a controls the operation of surgical stapler 100 by communicating, via the 1-wire communication chip 116d, with battery assembly 114, outer housing 112, adapter 120, and end effector 130 of surgical stapler 100. Switch board 116b is coupled to user-operable buttons mounted on outer housing 112 and communicates with microcontroller 116a to effect operation of surgical stapler 100 in accordance with the particular button or buttons depressed by the user. Motors 116c, in response to signals received from microcontroller 116a via the 1-wire communication chip 116d and power received from battery assembly 114, drive the mechanical operations of surgical stapler 100, e.g., to rotate, articulate, close, fire, and/or open end effector 130. Memory 116e stores information relating to inner assembly 113, i.e., battery assembly 114 and power-pack 116, such as identifying data, status data, usage data, operating programs, etc. Memory 116e may further store information relating to outer housing 112, adapter 120, and/or end effector 130 such as identifying data, setting data, status data, and usage data. User interface 116f is provided in the form of a display screen viewable from the exterior of outer housing 112 of handle assembly 110 and is configured to display information such as the operational status of surgical stapler 100, usage information associated with any or all of the components of surgical stapler 100, notifications, etc. Input/output 116g may be configured for wired connection and/or wireless communication with one or more external devices, e.g., charger 200, router 300, server 400, computer 500, smartphone or tablet 600, display monitor 700, etc., for communicating status information, usage data, updates, notifications, etc. therebetween.

Each of outer housing 112, adapter 120, and end effector 130 of surgical stapler 100 includes a memory 112a, 120a, 130a, respectively, storing information such as identifying data, setting data, and usage data. Utilizing the 1-wire communication chip 116d, microcontroller 116a of power-pack 116 is configured to access memories 112a, 120a, 130a when outer housing 112, adapter 120, and end effector 130, respectively, are attached to handle assembly 110. More specifically, microcontroller 116a reads the identifying data from memories 112a, 120a, 130a of outer housing 112, adapter 120, and end effector 130, respectively, and writes the same to memory 116e of power-pack 116 to enable tracking of that particular component and recognition upon subsequent attachment. Microcontroller 116a also reads the setting data from memories 112a, 120a, 130a of outer housing 112, adapter 120, and end effector 130, respectively, and matches the same to a corresponding use profile stored in memory 116e of power-pack 116 to ensure compatible operation of power-pack 116 in accordance with the particular configurations of the components attached thereto.

With respect to usage data, microcontroller 116a reads the usage data from memories 112a, 120a, 130a of outer housing 112, adapter 120, and end effector 130, respectively, and stores such usage data in memory 116e of power-pack 116 in connection with the identifying information for that component. Microcontroller 116a also stores usage data regarding inner assembly 113 in memory 116e. As detailed below, microcontroller 116 is further configured to update the usage data in its own memory 116e and/or in memories 112a, 120a, 130a of outer housing 112, adapter 120, and end effector 130, respectively, after each use, upon receipt of updating information, and/or periodically. Thus, memory 116e of power-pack 116 serves as a central repository for storing usage data relating to the various components used therewith, obviating the need for the individual components to output such usage data to an external device or devices. However, the usage data for each component is also stored locally in the memory of that component to enable use of each component with another power-pack 116.

Some of the components of surgical stapler 100 are configured as single-use components, e.g., outer housing 112 and end effector 130, although these components may alternatively be configured as reusable components. The usage data for such single-use components may indicate whether or not the component has been used. That is, after use, microcontroller 116a writes to memory 116e of power-pack 116 and memories 112a, 130a of outer housing 112 and end effector 130, respectively, that these components have been used. Accordingly, if outer housing 112 and/or end effector 130 is attempted to be used subsequently, microcontroller 116a would read the usage data indicating that these components have been used and, in response, provide an error notification and/or inhibit further operation until used components are connected.

Other components of surgical stapler 100, e.g., inner assembly 113 (which includes both battery assembly 114 and power-pack 116) and adapter 120, may be configured as reusable components defining a useful life measured by a number of uses, although other suitable metrics are also contemplated, e.g., number of sterilizations, in-use time, time-since-manufacturing, number of chargings, etc. With respect to these reusable components, the usage data thereof may include, for example, a usage counter indicating a number of times the component has been used, a maximum number of uses for the component, and a number of available usage credits for the component. After each use, microcontroller 116a updates the usage counters stored in memory 116e of power-pack 116 (for the use counters of inner assembly 113 and adapter 120) and memory 120a of adapter 120 (for the use counter of adapter 120). The maximum number of uses for inner assembly 113 and adapter 120 are pre-determined numbers stored in the memories 116e, 120e of power-pack 116 and adapter 120, although memory 116e of power-pack 116 may additionally store the maximum number of uses for adapter 120 in connection with the identifying information thereof. Microcontroller 116a decrements the number of available usage credits stored in the memories 116e, 120e for each of inner assembly 113 and adapter 120 after each use and updates the available usage credits upon receipt of a notification that additional usage credits have been applied to that particular inner assembly 113 and/or adapter 120.

Prior to entering a use mode, microcontroller 116a is configured to compare the use counter information for each component attached thereto with both the number of available usage credits for the component and the maximum number of uses for the component. As a result of this comparison, microcontroller 116a permits entry into a use mode, outputs a notification (to user interface 116f and/or to an external device via input/output 116g), and/or inhibits some or all functionality of surgical stapler 100. For example, where there are no available usage credits for any particular component or where the maximum number of uses for any particular component has been reached, microcontroller 116a may output an error notification and inhibit operation of surgical stapler 100. On the other hand, where each component has at least one available usage credit and has not reached its maximum number of uses, microcontroller 116a may permit entry into the use mode wherein full operation of surgical stapler 100 is permitted.

As noted above, the usage counter associated with each component is incremented in response to use of that component, while the maximum number of uses for each component is a pre-determined value stored in memory. Neither of these values are permitted to be tampered with, as they are intended to help ensure safe and effective operation of surgical stapler 100 by inhibiting use beyond certain limits. The number of available usage credits, however, is a variable that may be updated, reset, or changed in accordance with the number of usage credits purchased by the medical facility 10 and allocated to a particular component. These usage credits, together with the usage counters and maximum number of uses associated with a particular component, serve as the basis for the credit-based usage system of the present disclosure, which is described in greater detail below.

Referring again to FIG. 1, surgical stapler 100 and one or more of the devices within medical facility 10 and/or one or more of the devices within remote facility 20 may be utilized in accordance with the credit-based usage system of the present disclosure. Each of these devices will be generally described, followed by a more detailed description of the use of any of such devices, in conjunction with surgical stapler 100, in implementing the credit-based usage system of the present disclosure.

Charger 200 includes a base 210 defining a plurality of charging bays 220, each configured to receive a battery assembly 114 and a power-pack 116 (together as inner assembly 113 or separately from one another) of a surgical stapler 100, for enabling charging and/or data transfer therebetween. Charger 200 further includes a user interface 230 configured to display status information, usage data, notifications, etc. relating to an attached battery assembly 114, power-pack 116, or other component of surgical stapler 100 that has been previously used with the power-pack 116. For example, user interface 230 of charger 200 may be configured to display usage data relating to an attached power-pack 116, battery assembly 114, and an adapter 200 previously utilized therewith.

Router 300 may be configured as a hub that relays local communications, e.g., between surgical stapler 100, charger 200, server 400, computer 500, smartphone or tablet 600, and/or display monitor 700, and/or remote communications, e.g., between any of the devices of medical facility 10 and any of the devices of remote facility 20. Server 400 may be configured to transmit/receive data to/from any of the devices of medical facility 10 and/or any of the devices of remote facility 20 and to store such data in a database, process the data, etc. Router 300 and server 400 may include any suitable software, firmware, and hardware for these purposes.

Computer 500, smartphone or tablet 600, and display monitor 700 may be configured to receive data from surgical stapler 100, charger 200, server 400, and/or one another, e.g., via router 300, and to store such data in a database, process the data, and/or display the data on a respective display screen 510, 610, 710 thereof. These devices 500, 600, 700 may additionally or alternatively be configured to communicate with surgical stapler 100 and/or charger 200 for transmitting data thereto such as, for example, providing updated settings, parameters, operating code, programs, etc. Further, computer 500, smartphone or tablet 600, and display monitor 700 may be configured to communicate with any of the devices of remote facility 20. Devices 500, 600, 700 may include any suitable software, firmware, and hardware for these purposes.

Continuing with reference to FIG. 1, remote facility 20, as mentioned above, may include one or more servers 800 and one or more computers 900. Server 800 may be configured to receive data from any of the devices within medical facility 10 and/or to transmit data thereto. Server 800 may further be configured to store the data, process the data, and/or output the data to computer 900 or another device. Computer 900 may be configured to receive, store, process, and/or transmit data both locally, e.g., to server 800, and/or remotely, e.g., to any of the devices within medical facility 10. Server 800 and computer 900 may include any suitable software, firmware, and hardware for these purposes.

Figure 3:
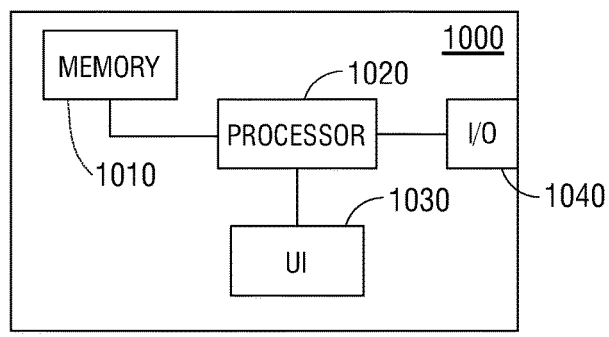
FIG. 3 is a schematic illustration of a device or devices configured for use with the system of FIG. 1.

Turning now to FIG. 3, one configuration of a system configured for use in conjunction with surgical stapler 100 and provided in accordance with the present disclosure is shown generally identified by reference numeral 1000. System 1000 generally includes a memory 1010, a processor 1020, a user interface (UI) 1030, and an input/output 1040. System 1000 may be embodied within one or more of charger 200, server 400, computer 500, smartphone or tablet 600, display monitor 700, server 800, computer 900, or other suitable device. For example, system 1000 may be fully embodied within charger 200, computer 500, or smartphone or tablet 600 as each of these devices includes a user interface 230 or display 510, 610, respectively, and appropriate hardware and software capability. As another example, memory 1010, processor 1020, and input/output 1040 of system 1000 may be embodied within one device, e.g., server 400, while user interface (UI) 1030 is embodied in a separate device in communication therewith, e.g., using display 710 of display monitor 700.

Memory 1010 of system 1000 may include any suitable component(s) operable for storing information such as operational data, usage data, status data, notifications, etc. for one or more surgical staplers 100 or other surgical instruments. Processor 1020 may include any suitable component(s), e.g., a central processing unit (CPU) and a storage unit, operable to execute instructions to receive, process, manipulate, and/or output the information. Input/output 1040 is provided to facilitate communication between system 1000, one or more surgical staplers 100 or other surgical instruments, and/or other devices via wires or wireless communication. More specifically, input/output 1040 allows for the receipt of information from surgical staplers 100, surgical instruments, or other devices, and for the transmission of information thereto. UI 1030 is provided to display the information received and allow for the input of data, instructions, settings, etc., by a user.

The credit-based usage system of the present disclosure may be implemented within inner assembly 113 of surgical stapler 100, or may be implemented across surgical stapler 100 and one or more additional devices, e.g., charger 200, server 400, computer 500, smartphone or tablet 600, display monitor 700, etc. More specifically, as noted above, inner assembly 113 of surgical stapler 100 and, more specifically, memory 116e of power-pack 116 stores usage counter information for itself and the various components utilized therewith and also stores other usage data indicating a maximum number of uses for itself and each component and a number of available usage credits for itself and each component. As detailed below, this usage data may be processed and displayed by surgical stapler 100 itself and/or may be output to one or more additional devices, e.g., charger 200, server 400, computer 500, smartphone or tablet 600, display monitor 700, etc., for processing and displaying the data. As also detailed below, surgical stapler 100 itself and/or one or more additional devices may further be configured to update the number of available usage credits for each component, thus permitting further use thereof (assuming the maximum number of uses has not been reached) in accordance with instructions to do so. These instructions may be provided from a local device within medical facility 10, may be transmitted from a remote device within remote facility 20, e.g., a manufacturer or supplier facility, or may be manually input into surgical stapler 100, e.g., via a salesperson visiting medical facility 10.

Referring now to FIGS. 4A-4G, in conjunction with FIGS. 1-3, a main display screen 1100 is shown displaying usage data relating to inner assembly 113 and adapter 200 of surgical stapler 100. Other data such as remaining battery power and connectivity strength is also provided in respective display sections 1120, 1130. Main display screen 1100 may represent user interface 116f of surgical stapler 100, user interface 230 of charger 200, display 510 of computer 500, display 610 of smartphone or tablet 600, display 710 of display monitor 700, or any other suitable display or user interface. The use and operation of the credit-based usage system of the present disclosure is detailed below and illustrated in the various displays of FIGS. 4A-4G; however, it is contemplated that various different forms of displays may be utilized, or that no display at all be provided. The underlying aspects and features of the credit-based usage system of the present disclosure remain applicable regardless of whether a particular display or any display at all is provided.

Main display screen 1100 is shown displaying icons 1040, 1050, 1060 representing handle assembly 110, adapter 120, and end effector 130 of surgical stapler 100. The information displayed on main display screen 110 is output from memory 116e of power-pack 116, as detailed above. More specifically, in area 1042, adjacent icon 1040 which represents handle assembly 110, the number of available usage credits for inner assembly 113 is provided. Similarly, in area 1052, adjacent icon 1050 which represents adapter 120, the number of available usage credits for adapter 120 is provided. Since end effector 130 and outer housing 112 are single-use components, no usage numbers are provided; however, if a used outer housing 112 and/or end effector 130 is attached (as determined by power-pack 116), a notification may be provided in the vicinity of icon 1040 or 1060, respectively, to indicate such. As detailed above, if use was attempted with a previously-used outer housing 112 or end effector 130, power-pack 116 would inhibit operation of surgical stapler 100 until the used component(s) is replaced with an unused component(s). Further, in areas 1044 and 1054 which are in the vicinity of icons 1040, 1050, respectively, the number of times inner assembly 113 has been used relative to the maximum number of uses thereof and the number of times adapter 120 has been used relative to the maximum number of uses thereof, respectively.

Figure 4A:
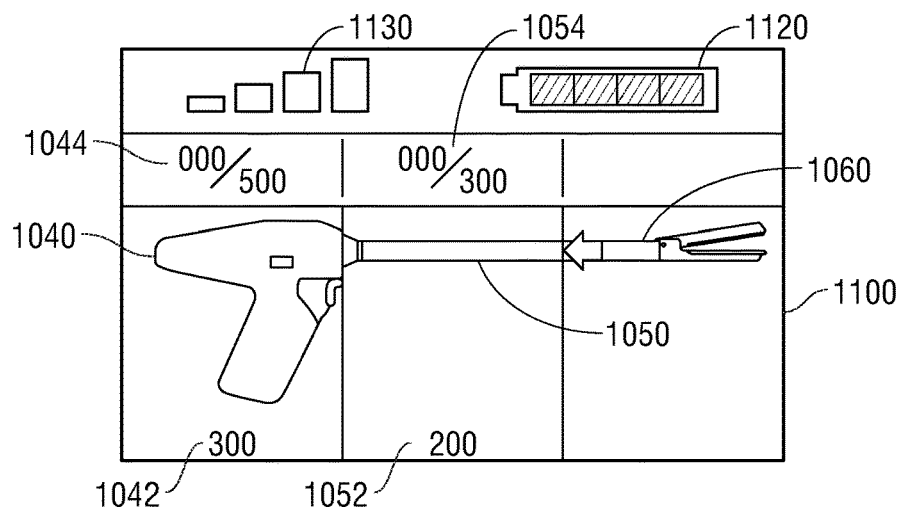
FIGS. 4A-4G are exemplary status display screens as displayed by a user interface or other display of an instrument or device of the system of FIG. 1.

FIG. 4A illustrates an initial condition of surgical stapler 100, wherein a new inner assembly 113 having a maximum of 500 uses, for example, is provided and an new adapter 120 having a maximum of 300 uses, for example, is provided. Further, for example, inner assembly 113 has been credited with 300 usage credits, while adapter 120, for example, has been credited with 200 usage credits. As detailed below, assignment of usage credits to inner assembly 113 and adapter 120 may be accomplished via the purchasing or transferring of usage credits thereto using one or more devices in communication with surgical stapler 100 or authorizing such directly to surgical stapler 100.

Figure 4B:
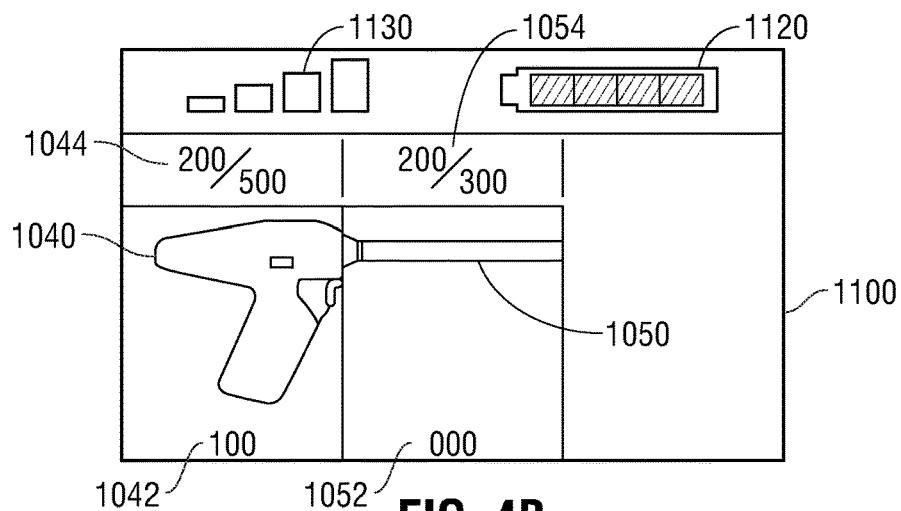

FIG. 4B illustrates main display screen 1100 showing the status of surgical stapler 100 after inner assembly 113 and adapter 120 have been used together for 200 uses, for example. Thus, area 1044 indicates that inner assembly 113 has been used 200 out of the maximum 500 uses, while area 1054 indicates that adapter 120 has been used 200 out of the maximum 300 uses. Further, area 1042 indicates that inner assembly 113 has 200 usage credits remaining, while area 1052 indicates that adapter 120 has no usage credits remaining. Again, this display information is received from power-pack 116 which, as detailed above, tracks and stores the usage counter, available usage credits, and maximum number of uses for each component used therewith.

With respect to the status shown in FIG. 4B, despite the fact that adapter 120 has yet to reach is maximum number of uses, further use of adapted 120 would be inhibited by power-pack 116 because adapter 120 does not have any remaining usage credits. As can be appreciated, the usage credit tracking feature of surgical stapler 100 may be used to limit the number of uses of a component thereof beyond a credited amount, which may be less than the maximum number of uses for that particular component. The user benefits in that the user can purchase a desired number of credits that is less than the maximum number of uses (and, thus, pay less), and the manufacturer or supplier benefits in that further use beyond this purchased number of credits can be inhibited (thus preventing fraudulent or un-paid use).

Figure 4C:
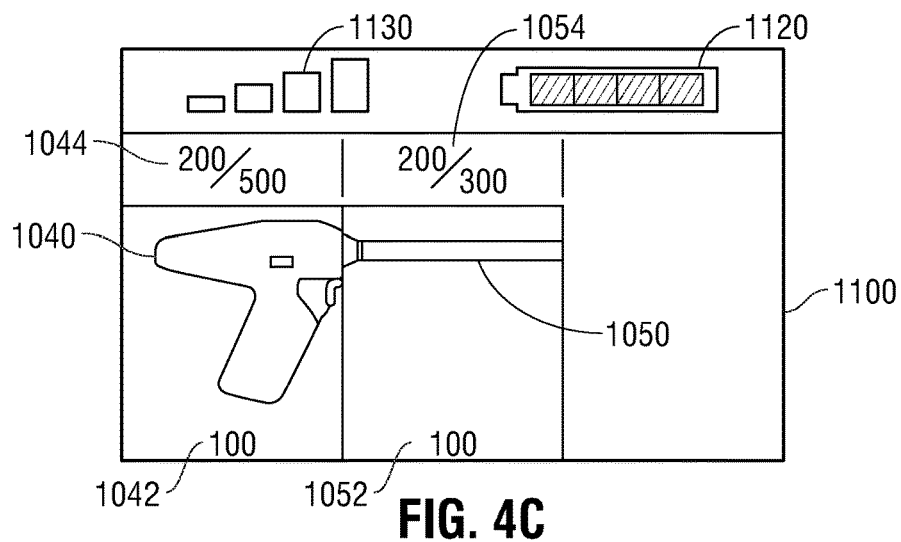

FIG. 4C illustrates main display screen 1100 showing the status of surgical stapler 100 after adapter 120 has been replenished, via purchase or transfer, with, for example, 100 usage credits.

Figure 4D:
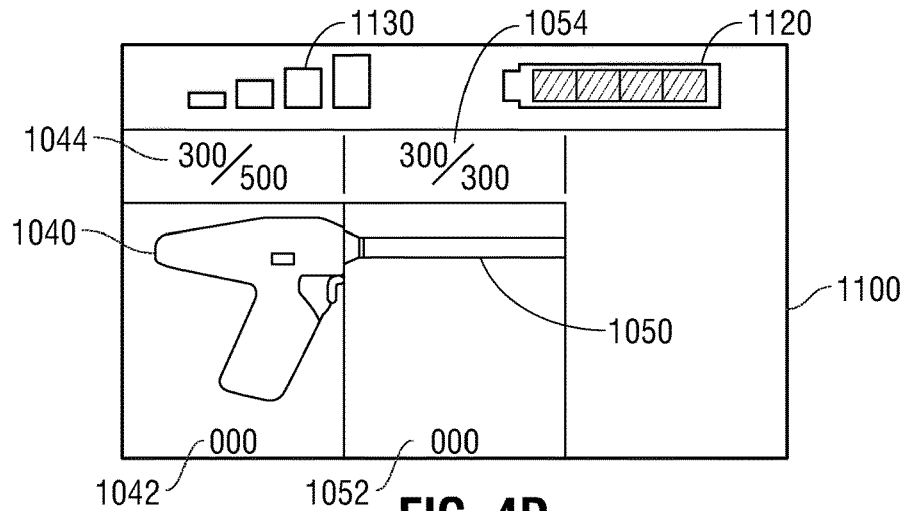

FIG. 4D illustrates main display screen 1100 showing the status of surgical stapler 100 after inner assembly 113 and adapter 120 have been used together for an additional 100 uses. Thus, area 1044 indicates that inner assembly 113 has been used 300 out of the maximum 500 uses, while area 1054 indicates that adapter 120 has reached the end of its usable life, i.e., adapter 120 has been used its maximum of 300 uses. Further, area 1042 indicates that inner assembly 113 has 100 usage credits remaining, while area 1052 indicates that adapter 120 has 100 usage credits remaining.

With respect to the status shown in FIG. 4D, adapter 120 is required to be replaced, while inner assembly 113 may either be replaced or replenished with additional usage credits, as no further usage credits are available for inner assembly 113.

Figure 4E:
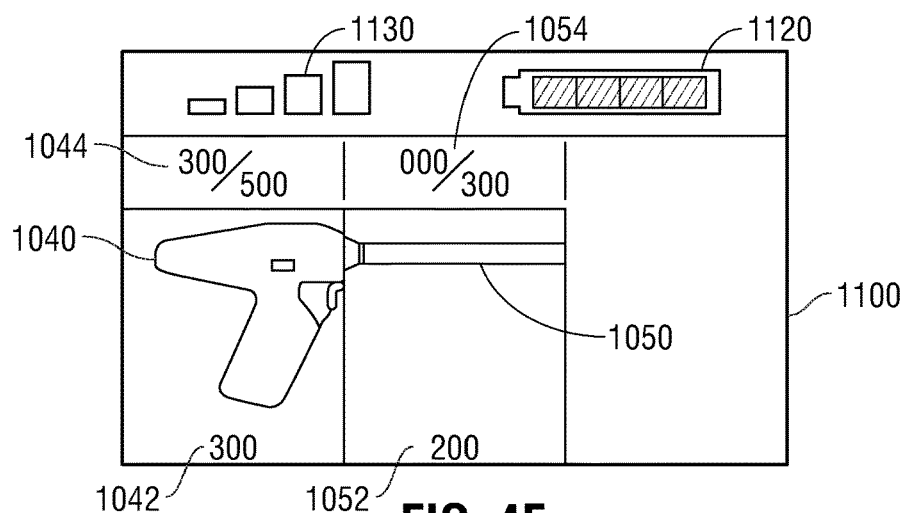

FIG. 4E illustrates main display screen 1100 showing the status of surgical stapler 100 after inner assembly 113 has been replenished with 300 use credits and a new, unused adapter 120 has been provided; the new, unused adapter 120 credited with 200 usage credits.

Figure 4F:
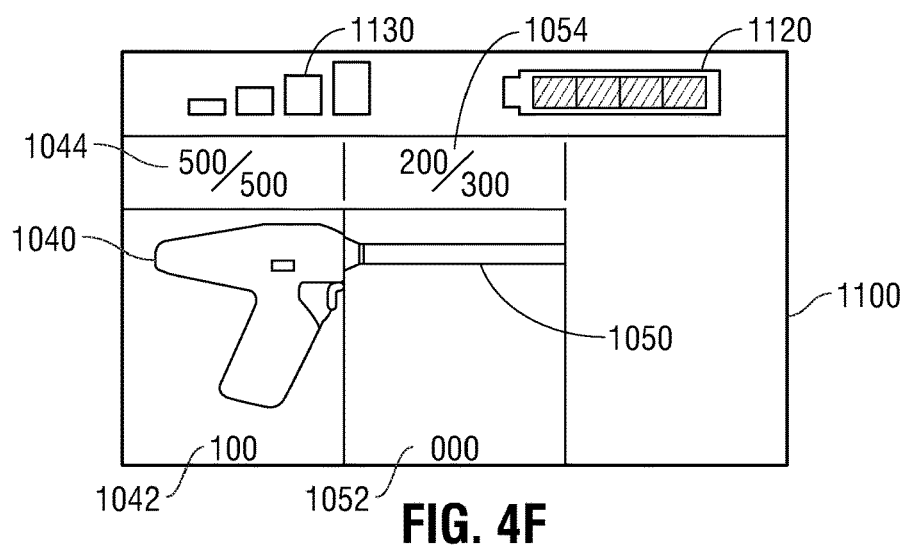

FIG. 4F illustrates main display screen 1100 showing the status of surgical stapler 100 after 200 further uses of inner assembly 113 with the new adapter 120. Thus, area 1044 indicates that inner assembly 113 has reached the end of its usable life, i.e., inner assembly 113 has been used the maximum 500 uses. Notably, despite the fact that inner assembly 113 has 100 usage credits available, inner assembly 113 cannot be used further and must be replaced since the maximum number of uses of inner assembly 113 has been reached. Area 1054 indicates that the new adapter has been used 200 out of its maximum of 300 uses. Further, as noted above, area 1042 indicates that inner assembly 113 has 100 usage credits remaining, while area 1052 indicates that adapter 120 has no usage credits remaining. Thus, adapter 120 must either be replaced or replenished with additional usage credits, prior to further use.

Figure 4G:
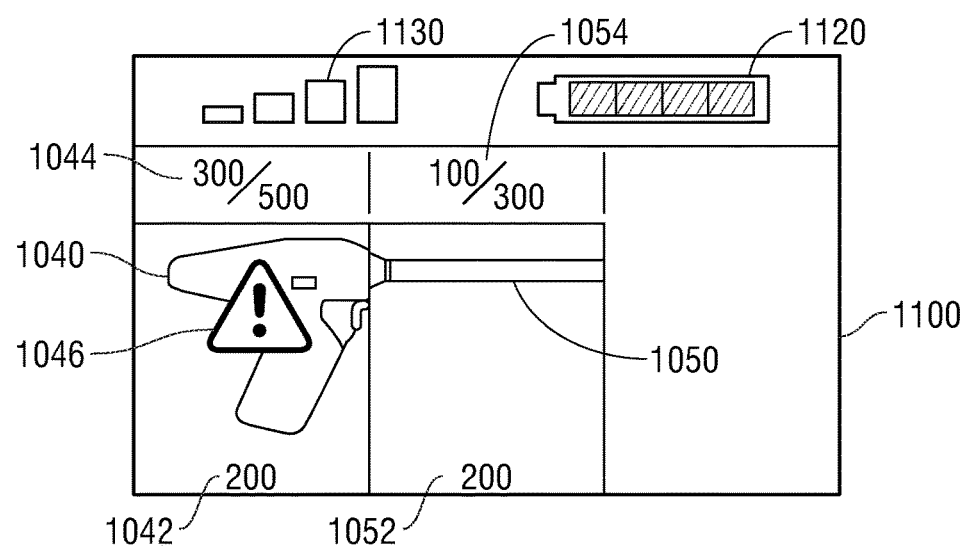

FIG. 4G illustrates main display screen 1100 showing the status of surgical stapler 100 after an error has been detected within inner assembly 113, as indicated by power-pack 116 and/or battery assembly 114. As such, an error icon 1046, displayed in response to a notification of such output from power-pack 116, is provided. In this situation, despite the fact that usable life and usage credits remain for inner assembly 113, power-pack 116 inhibits further use of inner assembly 113 due to the error and, accordingly, such is displayed on main display screen 1100. Thus, inner assembly 113 must be repaired and/or replaced before being used again.

Figures 5, 6A, 6B:
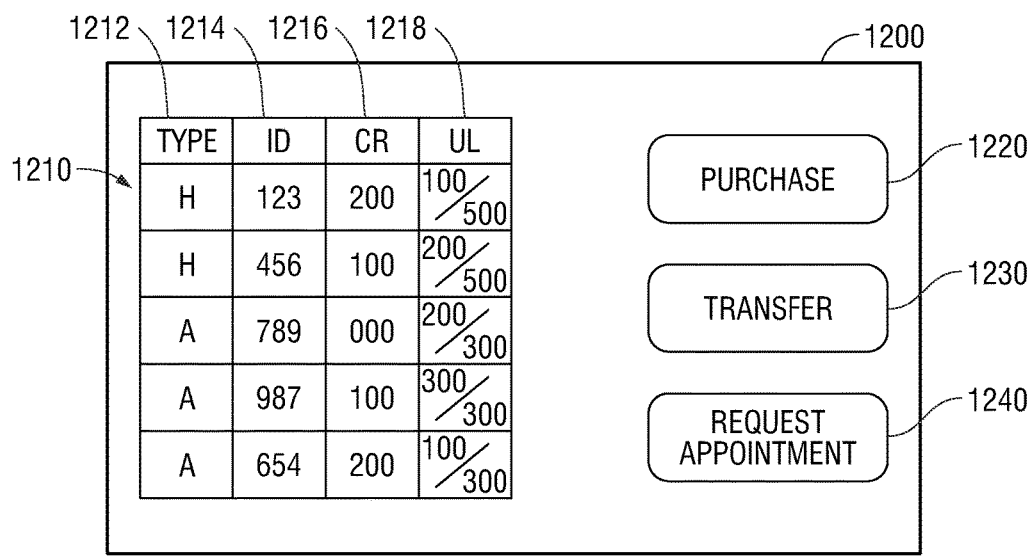
FIG. 5 is an exemplary inventory display screen as displayed by a user interface or other display of an instrument or device of the system of FIG. 1.
FIG. 6A is an exemplary purchasing display screen as displayed by a user interface or other display of an instrument or device of the system of FIG. 1.
FIG. 6B is an exemplary transferring display screen as displayed by a user interface or other display of an instrument or device of the system of FIG. 1.

Turning now to FIG. 5, in conjunction with FIGS. 1-3, as mentioned above, usage credits may be purchased and/or transferred to/from a particular component of surgical stapler 100 to allow for replenishment of usage credits, removal of usage credits from no-longer-usable components, or for other reasons. FIG. 5 illustrates a status display screen 1200 that may represent display 510 of computer 500, display 610 of smartphone or tablet 600, the display of computer 800, or any other suitable display or user interface. Status display screen 1200 displays to the user the present inventory, the number of usage credits remaining for each component, and the remaining useable life of each component. More specifically, status display screen 1200 provides a table 1210 having a first column 1212 indicating the type of components in inventory, a second column 1214 indicating the identification number or code for each component (which is also stored in the memory thereof), a third column 1216 indicating the number of usage credits remaining for each component, and a fourth column 1218 indicating the remaining useable life of each component. As can be appreciated, using this information, a user can view the status of each component in inventory, determine whether it is necessary to purchase additional usage credits, and/or whether it is necessary to transfer usage credits between components.

As an alternative to allocating usage credits to a particular component, it is also contemplated that purchased usage credits for a particular type of component be universally applied to all such components in inventory. In such an embodiment, the above-detailed function of the credit-based usage system of the present disclosure would function similarly except that the various surgical staplers 100 would communicate with one another or with a common device to enable updating of the available usage credits for each component type in the memories of each stapler 100 and/or device 200, 400, 500, 600, 700, 800, 900.

Continuing with reference to FIG. 5, in conjunction with FIGS. 1-3, status display screen 1200 also provides icons 1220, 1230, 1240 that link to a purchase display screen 1300 (FIG. 6A), a transfer display screen 1400 (FIG. 6B), and to a request for appointment screen (not shown), respectively. It is envisioned that the device displaying status display screen 1200 be capable of communication with the surgical stapler(s) 100 or other surgical instrument(s) within medical facility 10 to receive up-to-date usage information regarding the components thereof.

Purchase display screen 1300 is illustrated in FIG. 6A, and may represent display 510 of computer 500, display 610 of smartphone or tablet 600, the display of computer 800, or any other suitable display or user interface. Using purchase display screen 1300, a user is able to select a desired number of usage credits for each particular component, view the costs thereof, and purchase such usage credits. Upon purchasing usage credits, payment is transmitted to the manufacturer or supplier and, in turn, information is sent to surgical stapler(s) 100 and/or devices 200, 400, 500, 600, 700, 800, and/or 900 to update the available usage credits corresponding to those components for which usage credits were purchased.

Transfer display screen 1400 is illustrated in FIG. 6B, and may represent display 510 of computer 500, display 610 of smartphone or tablet 600, the display of computer 800, or any other suitable display or user interface. Transfer display screen 1400 is provided to enable transfer of usage credits from one component to another component of the same type. Transferring usage credits may be desired where a component has remaining usage credits associated with it despite the component being at the end of its usable life, where an error has occurred with a component rendering it no longer usable despite having usage credits remaining, or simply where it is desired to redistribute the usage credit distribution among the similar components.

Referring again to FIG. 5, the request an appointment icon 1240, as noted above, allows the medical facility to schedule a visit from a salesperson at which time usage credits can be purchased, components can be purchased and/or returned, and the transfer of usage credits can be accomplished. Further, as opposed to the above-detailed automated or partially-automated purchase and transfer of usage credits, the same may also be accomplished in manual fashion, e.g., via a salesperson visiting medical facility 10. Automatic replenishments are also contemplated, for example, wherein 50 usage credits are applied to a particular component and charged to the medical facility 10 every month, for the life of that particular component.

As can be appreciated in view of the foregoing, the credit-based usage system of the present disclosure serves as a use limiter that limits the use of a particular component or device to a number of uses equal to or less than the maximum number of uses of the device. Thus, a medical facility 10 is not bound to costs associated with the maximum number of uses but, rather, may pay for a number of uses determined by the medical facility 10. Further, by allowing for replenishment, the medical facility 10 may spread capital costs over the life of the component rather than having a large initial capital investment, even where full use of the component is expected. Thus, the credit-based usage system of the present disclosure provides greater flexibility in terms of device usage, capital outlay and resource management as compared with traditional sales regimes.

The credit-based usage system of the present disclosure is detailed above as determining use of a component by incrementing a use counter. This may be accomplished upon engagement of the component with surgical stapler 100, upon firing of surgical stapler 100, upon disengagement of the component from surgical stapler 100, upon sterilization of the component, upon charging of inner assembly 113, or in response to any other suitable condition or event. As an alternative to counter-based use determination, time-based use may also be utilized. In such embodiments, the credit-based usage system would operate similarly as detailed above except that, rather than utilizing counters, each component would include a use time tracker, define a maximum amount of use time, and include a usage credit time stored therein, which may be transferred and/or replenished similarly as detailed above. Combinations of counter and time-based systems are also contemplated.

Although embodiments have been described in detail with reference to the accompanying drawings for the purpose of illustration and description, it is to be understood that the present disclosure is not to be construed as limited thereby. It will be apparent to those of ordinary skill in the art that various modifications to the foregoing embodiments may be made without departing from the scope of the disclosure.

What is claimed is:

1. A surgical system, comprising:
   a plurality of surgical instruments, each of the plurality of surgical instruments including:
   a reusable component;
   a processor;
   a non-transitory computer-readable storage medium storing instructions that, when executed by the processor, cause the processor to monitor usage of the reusable component; and
   a local memory,
   wherein an overall available usage credit is stored in the local memory of each of the plurality of surgical instruments; and
   a central device in communication with each of the plurality of surgical instruments, the central device including a central memory storing the overall available usage credit, a central processor, and a central non-transitory computer-readable storage medium storing instructions that, when executed by the central processor, cause the central processor to communicate with the processor of each of the plurality of surgical instruments such that, upon use of the reusable component of any one of the plurality of surgical instruments, the overall available usage credit stored in the central memory and in each of the local memories is decreased accordingly.

2. The surgical system according to claim 1, further comprising a display screen, wherein the central processor is further caused to communicate with the display screen to display status information regarding the overall available usage credit on the display screen.

3. The surgical system according to claim 2, wherein the display screen is associated with the central device.

4. The surgical system according to claim 2, wherein the display screen is associated with one of the plurality of surgical instruments.

5. The surgical system according to claim 1, wherein the central processor of the central device is further caused to communicate with the processor of each one of the plurality of surgical instruments to increase the overall available usage credit stored in the local memory thereof upon receiving instructions to replenish the overall available usage credit.

6. The surgical system according to claim 5, wherein the instructions to replenish are provided in response to the purchase of additional usage credit.

7. The surgical system according to claim 1, wherein the overall available usage credit is measured in number of uses.

8. The surgical system according to claim 1, wherein the overall available usage credit is measured in time of use.

9. The surgical system according to claim 1, wherein the overall available usage credit is decreased upon engagement of one of the reusable components with the surgical instrument thereof.

10. The surgical system according to claim 1, wherein the overall available usage credit is decreased upon disengagement of one of the reusable components from the surgical instrument thereof.

11. The surgical system according to claim 1, wherein the overall available usage credit amount is decreased in response to firing of one of the surgical instruments.

12. The surgical system according to claim 1, wherein the reusable component of each of the plurality of surgical instruments includes a pre-defined maximum usage amount, and wherein use of one of the reusable components is inhibited when the pre-defined maximum usage amount thereof is reached regardless of the overall available usage credit remaining.

13. The surgical system according to claim 1, wherein at least one of the plurality of surgical instruments further includes a single-use component.

* * * * *